(12) United States Patent
Grant et al.

(10) Patent No.: US 8,551,002 B2
(45) Date of Patent: Oct. 8, 2013

(54) SPATIAL ARRAY OF SENSORS MOUNTED ON A TOOL

(75) Inventors: Danny A. Grant, Laval (CA); Juan Manuel Cruz-Hernandez, Montreal (CA); Christopher J. Ullrich, Santa Cruz, CA (US)

(73) Assignee: Immersion Corporation, San Jose, CA (US)

( * ) Notice: Subject to any disclaimer, the term of this patent is extended or adjusted under 35 U.S.C. 154(b) by 1332 days.

(21) Appl. No.: 12/333,600

(22) Filed: Dec. 12, 2008

(65) Prior Publication Data

US 2010/0152586 A1 Jun. 17, 2010

(51) Int. Cl.
*A61B 8/00* (2006.01)

(52) U.S. Cl.
USPC .......................... 600/459; 600/437

(58) Field of Classification Search
USPC .......................... 600/459; 604/22
See application file for complete search history.

(56) References Cited

U.S. PATENT DOCUMENTS

| | | | |
|---|---|---|---|
| 5,619,180 A | 4/1997 | Massimino et al. | |
| 5,833,634 A | 11/1998 | Laird et al. | |
| 5,967,990 A * | 10/1999 | Thierman et al. | 600/459 |
| 5,989,199 A | 11/1999 | Cundari et al. | |
| 2002/0143275 A1 | 10/2002 | Sarvazyan et al. | |
| 2007/0049973 A1 | 3/2007 | Burbank et al. | |
| 2007/0197895 A1* | 8/2007 | Nycz et al. | 600/407 |
| 2009/0234273 A1* | 9/2009 | Intoccia et al. | 604/22 |

FOREIGN PATENT DOCUMENTS

| | | |
|---|---|---|
| DE | 4332580 | 3/1995 |
| DE | 19527957 | 8/1996 |
| WO | WO-01/39668 A1 | 6/2001 |
| WO | WO-02/07617 A2 | 1/2002 |
| WO | WO-2005/094672 A1 | 10/2005 |
| WO | WO-2008/082992 A1 | 7/2008 |

OTHER PUBLICATIONS

Ottermo, Maria V. et al. Palpation Instrument for Augmented Minimally Invasive surgery. Sep. 28, 2004. Proceedings of 2004 IEEE/RSJ International Conference on Intelligent Robots and Systems. pp. 3960-6964.*

International Search Report, Int'l Appl No. PCT/US2009/066908 Mar. 16, 2010.

Ottermo, Maria Vatshaug, Virtual Palpation Gripper, A Dissertation Submitted in Partial Fulfillment of the Requirements for the Degree of Philosophiae Doctor, PhD, Department of Engineering Cybernetics, Norwegian University of Science and Technology, 2006, i-viii and 1-139.

(Continued)

*Primary Examiner* — Peter Luong
(74) *Attorney, Agent, or Firm* — Medler Ferro PLLC

(57) ABSTRACT

Systems and methods described herein include an array of sensors positioned on a tool. In one embodiment, among others, a tool includes a handle configured to be manipulated by a user. The tool also includes an end portion arranged in mechanical communication with the handle. In addition, the tool includes an array of sensors mounted on the end portion, in which the array of sensors is configured to sense a property of an object. The tool also comprises a processing device configured to process the properties of the object sensed by the array of sensors and to obtain spatial information of the object. The processing device is further configured to communicate the spatial information to the handle.

17 Claims, 3 Drawing Sheets

(56) References Cited

OTHER PUBLICATIONS

Miller, Andrew P., et al., Tactile Imaging System for Localizing Lung Nodules during Video Assisted Thoracoscopic Surgery, 2007 IEEE International Conference on Robotics and Automation, Roma, Italy, Apr. 10-14, 2007, 2996-3001.

Howe, Robert D., et al., Remote Palpation Technology for Surgical Applications, IEEE Engineering in Medicine and Biology Magazine, 14(3):318-323, 1995, 1-15.

Beasley, Ryan A., et al., Tactile Tracking of Arteries in Robotic Surgery, Proceedings of the 2002 IEEE International Conference on Robotics & Automation, Washington, DC, May 2002, 3801-3806.

* cited by examiner

SPATIAL ARRAY OF SENSORS MOUNTED ON A TOOL

TECHNICAL FIELD

The embodiments of the present disclosure generally relate to hand tools and more particularly relate to mounting an array of sensors on an end of a hand tool.

BACKGROUND

As opposed to open surgery in which a surgeon cuts a relatively large incision in the skin of a patient for accessing internal organs, minimally invasive surgical procedures are performed by making relatively small incisions and then inserting tools through the incisions to access the organs. Minimally invasive surgery usually results in shorter hospitalization times, reduced therapy requirements, less pain, less scarring, and fewer complications.

During minimally invasive surgery, a surgeon can introduce a miniature camera through an incision. The camera transmits images to a visual display, allowing the surgeon to see the internal organs and tissues and to see the effect of other minimally invasive tools on the organs and tissues. In this way, the surgeon is able to perform laparoscopic surgery, dissection, cauterization, endoscopy, telesurgery, etc. Compared to open surgery, however, minimally invasive surgery can present limitations regarding the surgeon's ability to see and feel the patient's organs and tissues.

SUMMARY

The present disclosure describes a number of embodiments in which an array of sensors is positioned on an end of a tool. Specifically, in one particular embodiment, a tool is defined as having a handle configured to be manipulated by a user. The tool includes an end portion arranged in mechanical communication with the handle. An array of sensors is mounted on the end portion and is configured to sense a property of an object. The tool also comprises a processing device configured to process the properties of the object sensed by the array of sensors and to obtain spatial information of the object. The processing device is further configured to communicate the spatial information to the handle.

The embodiments described in the present disclosure may include additional features and advantages, which may not necessarily be expressly disclosed herein but will be apparent to one of ordinary skill in the art upon examination of the following detailed description and accompanying drawings. It is intended that these additional features and advantages be included within the present disclosure.

BRIEF DESCRIPTION OF THE DRAWINGS

The components of the following figures are illustrated to emphasize the general principles of the present disclosure and are not necessarily drawn to scale. Reference characters designating corresponding components are repeated as necessary throughout the figures for the sake of consistency and clarity.

DETAILED DESCRIPTION

Although minimally invasive surgical procedures involving small incisions include many advantages over open surgery, minimally invasive surgery can still create challenges to a surgeon. For example, the surgeon must typically rely on a camera to view the patient's internal organs and see how the movement and operation of the tools affects the organs. Also, the surgeon is usually unable to palpate or receive tactile feedback with respect to the stiffness and/or pulsation of organs. To overcome the inherent limitation regarding touch, it can be beneficial to re-introduce the surgeon to the concept of palpation by providing tactile or haptic feedback in some manner in order to communicate better the sensation and feel of the patient's organs to the surgeon.

The present disclosure describes embodiments that include any type of tools that can be manipulated by a user. More particularly, the tools described in the present disclosure include a handle portion that mechanically controls an end portion of the tool. Mounted on the end portion is an array of sensors for sensing a property of an object that interacts with the tool. Using the information from the multiple sensors, additional properties of the object can be determined. For instance, the spatial relationship of the different sensors can be used to determine spatial information. Likewise, both spatial and temporal relationships of the sensed properties at the different sensors over time can also be used to determine specific information about the object.

Although many of the examples described in the embodiments of the present disclosure relate to surgical hand tools, such as minimally invasive surgical tools, it should be understood that the present disclosure also encompasses other types of tools as well. In addition, although many of examples herein relate to a surgical patients and how the organs and tissues of the patient interact with the surgical tools, it should also be understood that the present disclosure also includes other objects, which are normally intended to interact with the respective tools. Other features and advantages will be apparent to one of ordinary skill in the art upon reading and understanding the general principles of the present disclosure and are intended to be included herein.

Figure 1:
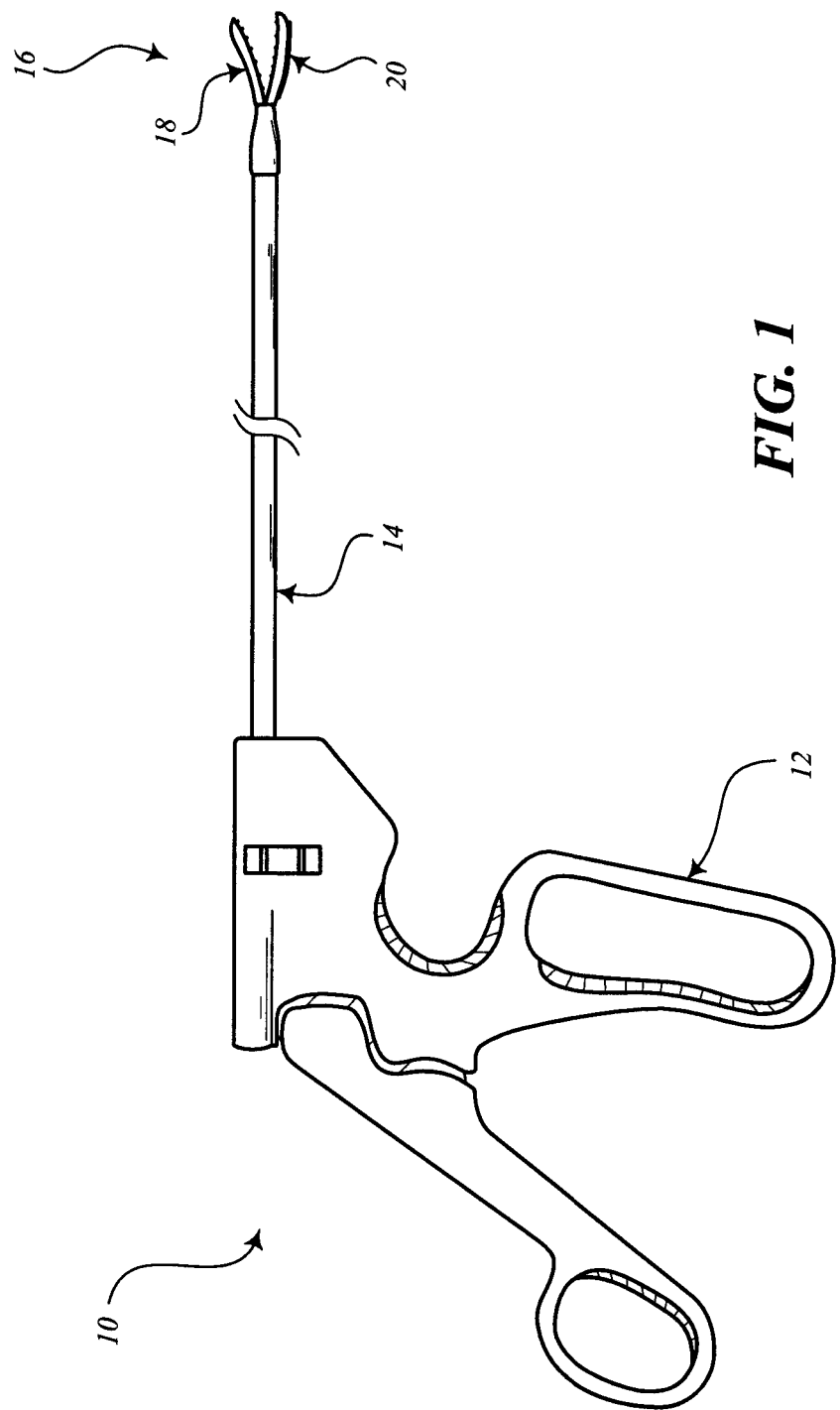
FIG. 1 is a diagram of a surgical hand tool having a sensor array, according to one embodiment.

FIG. 1 illustrates an embodiment of a surgical tool 10. In this diagram, surgical tool 10 is shown as a hand-held laparoscopic tool, which is configured to be inserted through a small incision in the abdomen of a patient. Surgical tool 10 in this embodiment includes a handle 12, a shaft 14, and an end portion 16. Shaft 14 is designed to connect handle 12 to end portion 16 and to communicate mechanical actions of handle 12 to end portion 16. Shaft 14 is further designed to communicate electrical signals from end portion 16 back to handle 12 as explained in more detail below. According to the embodiment of FIG. 1, end portion 16 includes a tip 18 and a sensor array 20 formed on tip 18. As shown, tip 18 is a grasper. However, it should be understood that end portion 16 may include any suitable type of tip having any suitable functionality. Also, in other alternative embodiments, sensor array 20 may be connected a portion of end portion 16 other than tip 18. According to some examples of the embodiment of FIG. 1, shaft may be about 20 cm to 30 cm in length and tip 18 may be about 10 mm to 15 mm in length.

By manipulating handle 12, a user can insert end portion 16 into the abdomen of the patient and control tip 18 of end portion 16. When end portion 16 is inserted, the surgeon can further manipulate handle 12 to control the location and orientation of tip 18 such that sensor array 20 is able to contact certain regions of the patient. Sensor array 20 can measure or test any desired property or parameter of the patient, such as, for example, pulse. In some embodiments in which sensor array 20 does not necessarily need to contact a particular region, tip 18 can be controlled to position sensor array 20 to accomplish certain contactless sensing.

Figure 2:
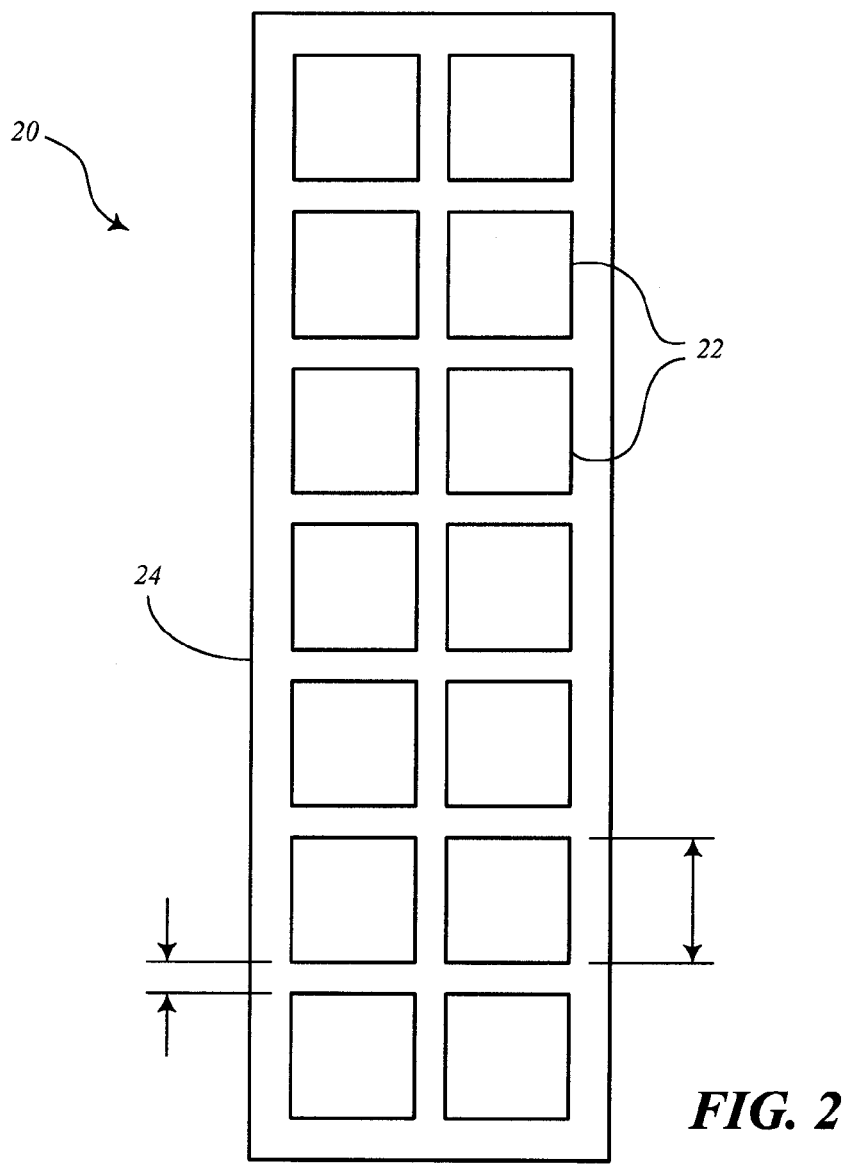
FIG. 2 is a diagram of the sensor array shown in FIG. 1, according to one embodiment.

FIG. 2 is a diagram illustrating an embodiment of sensor array 20 shown in FIG. 1. Sensor array 20 includes a number of sensors 22 connected to a substrate 24, which is configured to hold sensors 22 in a pattern having a predetermined pitch between sensors 22. As shown in this diagram, sensor array 20 includes seven rows and two columns of sensors 22 from the perspective of handle 12 (FIG. 1). It should be understood, however, that sensor array 20 can be arranged to include any number of rows and columns. In some embodiments, sensors 22 may be arranged in a pattern that does not particularly resemble a rectangular array. For example, sensors 22 can be positioned is a staggered pattern, circular pattern, etc.

Although sensors 22 are illustrated as being square, sensors 22 may include any suitable shape, e.g., rectangular, circular, elliptical, etc. According to the embodiment of FIG. 2 in which sensors 22 are square, sensors 22 may have widths and lengths of about 2 mm and may be separated by a distance of about 0.5 mm. In some embodiments, the size of sensors 22 may be smaller to allow a greater number of sensors to be positioned in sensor array 20. The size and number of sensors 22 may depend, for example, on the ability to miniaturize the particular type of sensor while keeping the integrity and usefulness of the sensor. If miniaturization techniques are used, the array of sensors 22 may include dozens of rows and columns of sensors 22. Sensors 22 may also be of any size and shape on substrate 24.

Sensors 22 can be configured to sense any suitable property of the object under test. For instance, sensors 22 can be configured as pressure sensors using resistive or capacitive pressure sensing technologies. Alternatively, sensors 22 can include strain gauges, piezoelectric sensors, stiffness sensors, etc. As strain gauges, sensors 22 can provide additional information about contact force to finely tune a generally course measurement of force. As piezoelectric sensors, sensors 22 can generate ultrasound signals that reflect off portions of the object. In this case, echo signals can be detected by sensors 22 to determine the location of objects. The ultrasound emission and echo measurement technique may be particularly useful for sensing the location of luminal structures and for tumor tissue identification. Sensors 22 can also be configured as stiffness sensors that can detect nodules, e.g., tumors, or other stiff regions. By processing the number of sensors 22 contacting the stiff region, a calculation can be made regarding the size of the nodules. In this respect, the number of sensors 22 that sense relative stiffness can be used to determine the size of the nodule and thereby increase or decrease an output signal provided to the user to communicate the size.

By using multiple sensors 22, greater accuracy can be assured of a property being measured than if only a single sensor were used. This also can increase the confidence when adjacent sensors 22 provide the same or similar outputs. Also, sensor array 20 can provide information indicative of the size of a particular feature, e.g., nodule, of the patient.

Substrate 24 may include any suitable structure for supporting sensors 22 on tip 18 (FIG. 1). Depending on the size, shape, and rigidity of tip 18, substrate 24 may be rigid or flexible to conform to tip 18. Also, substrate 24 may be planar or curved depending on the structure of tip 18. In the embodiment of FIG. 1 in which tip is a metal grasper with a curved bottom jaw, substrate 24 may be curved to conform to the curved shape of the bottom jaw. Also, since the jaw is substantially rigid, substrate 24 does not necessarily need to be rigid to provide needed support for sensors 22 and therefore can be flexible.

Figure 3:
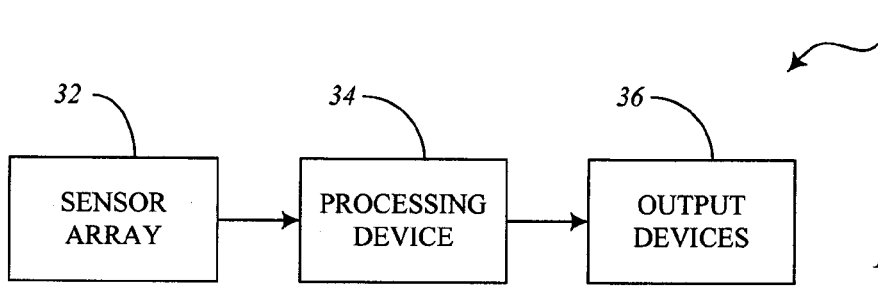
FIG. 3 is a block diagram of a system for communicating sensed properties to a user, according to a first embodiment.

FIG. 3 is a block diagram illustrating an embodiment of a system 30 for communicating spatial information about an object to a user. In this embodiment, system 30 includes a sensor array 32, processing device 34, and output devices 36. In some embodiments, system 30 contains sensor array 32, processing device 34, and output devices 36 on a hand-held tool or device. Particularly, sensor array 32 may be positioned on a portion of a tool, e.g., a tool used for probing an object. Sensor array 32 is configured to include any type of sensing mechanisms to sense any suitable characteristic of the object. The sensed information from each sensor is communicated to processing device 34, which is configured to process the information according to specific algorithms. Depending on the type of sensing mechanisms of sensor array 32 and the type of properties being measured, the algorithms of processing device 34 can determine various characteristics of the object. Processing device 34 may then communicate the processed information to output device 36, which is designed to present the information to the user in any suitable manner.

Sensor array 32 may represent any suitable sensor array positioned on an end of a tool for detecting one or more specific properties of an object. For instance, sensor array 32 may be the same as or similar to sensor array 20 described with respect to FIGS. 1 and 2. Particularly, sensor array 32 includes a plurality of sensors, each capable of measuring properties of an object at predefined locations with respect to the other sensors. Based on spatiality of sensors of sensor array 32, processing device 34 can determine or infer spatial information about the object. Processing device 34 may include different types of algorithms for extracting the particular information needed to calculate the spatial information.

According to one example, a surgeon may use a tool having sensor array 32 positioned on the tool for measuring pulse. When pulse information is detected along a row of sensors in the array but no pulse information is detected on the other sensors, then processing device 34 may be configured to deduce that a blood vessel is positioned or oriented in that particular direction including that row of sensors where the pulse is detected. On the other hand, if pulse information is detected along a column or across a diagonal, then the position or orientation of a blood vessel can be inferred accordingly.

Furthermore, in addition to spatial inferences, processing device 34 can also use any changes of the sensed information over time to extract temporal information. Particularly, the signals can be detected in real time to allow the processing of time-related signals. For example, processing device 34 may be able to detect peaks in the signals to determine when the signal is at its highest or lowest point. Also, processing device 34 can detect phase differences, etc. In some embodiments, processing device 34 may be configured to use the spatial and temporal information to detect not only the orientation of blood vessels, but also the direction in which the blood flows through the vessels. For example, pulse information can be detected at one instance of time and detected again along the path of the vessel at a later instance.

It has also been observed that when a blood vessel is pulsating, the sensors against which the blood vessel is in contact can sense the pulse. In addition, the sensors adjacent to those sensors that are in contact with the vessel can experience a loss of contact with tissue due to the lifting action of the pulsing vessel on the contacted sensors. In this case, the adjacent sensors may produce a signal that is 180 degrees out of phase with the pulse detecting sensors. Processing device 34 can be configured to detect this phenomenon to determine the location of blood vessels and for detecting pulse information.

Processing device 34 may be a general-purpose or specific-purpose processor or microcontroller for processing the signals detected by sensor array 32. In some embodiments, processing device 34 may include a plurality of processors for performing different functions with respect to system 30. In some embodiments, processing device 34 may be associated with a memory device (not shown) for storing data and/or instructions. In this regard, the memory may include one or more internally fixed storage units, removable storage units, and/or remotely accessible storage units, and the various storage units may include any combination of volatile memory and non-volatile memory. Logical instructions, commands, and/or code can be implemented in software, firmware, or both, and stored in memory. In this respect, the logic code may be implemented as one or more computer programs that can be executed by processing device 34.

In other embodiments, logical instructions, commands, and/or code can be implemented in hardware and incorporated in processing device 34 using discrete logic circuitry, an application specific integrated circuit ("ASIC"), a programmable gate array ("PGA"), a field programmable gate array ("FPGA"), etc., or any combination thereof. In yet other embodiments, logical instructions, commands, and/or code can be implemented in both hardware in processing device 34 and software/firmware stored in the memory.

Output devices 36 may include one or more mechanisms for communicating to a user information sensed by sensor array 32 and processed by processing device 34. Output devices 36 may include any suitable combination of display screens, speakers, tactile actuators, haptic effect devices, or other notification devices. Thus, output devices 36 may include any number of feedback mechanisms in any number of modes for providing any type of visual, audible, and/or tactile output to the user. In the embodiments regarding surgical tools, output devices 36 may be used to provide feedback to the surgeon so that the surgeon can reposition the tool as necessary to align, orient, or position the tool to allow the sensing of a more reliable signal, to reduce pressure on particular organs, etc.

In some embodiments, output devices 36 can include haptic actuators, which is able to generate a vibration on handle 12. The haptic actuators, for example, can include one or more force applying mechanisms that are configured to apply a vibrotactile force to a user of surgical tool 10 or other device. The haptic actuators may include electromagnetic actuators, eccentric rotating mass ("ERM") actuators in which an eccentric mass is moved by a motor, linear resonant actuator ("LRA") in which a mass attached to a spring is driven back and forth, a "smart material" such as piezoelectric, electroactive polymers or shape memory alloys, or other suitable type of actuating device.

Figure 4:
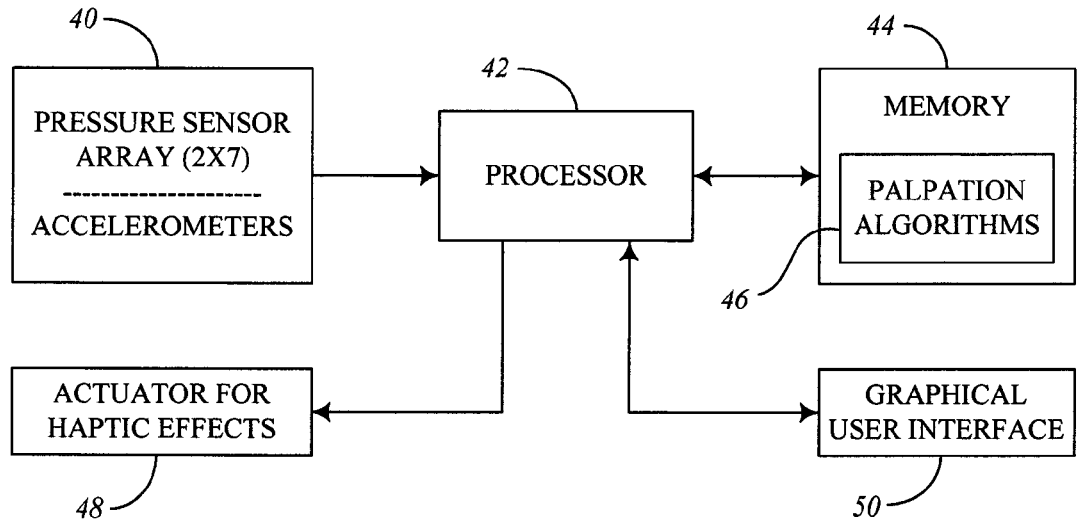
FIG. 4 is a block diagram of a system for communicating sensed properties to a user, according to a second embodiment.

FIG. 4 illustrates a system block diagram for a computer-assisted hand tool in which palpation algorithms can be deployed in an exemplary embodiment. The computer-assisted hand tool includes a plurality of sensors 40, which could include accelerometers for detecting and measuring the acceleration of a tool, and a pressure sensor array for detecting pulses during movement of the tip of the tool on the tissue being palpated. Processor 42 receives signals from sensors 40 and processes the received signals based on instructions stored in memory 44, which may include, among other things, palpation algorithms 46.

Based on a "state" of a tool determined during execution of palpation algorithms 46, processor 42 can cause an actuator 48 of the tool to play a haptic effect. It should be noted that the term "haptic effect" can refer to a tactile effect, tactile feedback, haptic feedback, force feedback, vibrotactile feedback, haptic cues, thermal feedback, kinesthetic feedback, etc. Generally, haptic effect can include the representation of any physical properties (e.g., stiffness, viscosity, etc.). The haptic effect played is characterized by one or more of the magnitude, frequency, and duration of the effect. The haptic effect can be dynamic based on a changing level of stiffness or deformation of the tissue being examined.

In some embodiments, processor 42 can be a laptop or personal computer that is electrically coupled to the tool. The laptop or personal computer can have a graphical user interface (GUI) 50 that enables the user to select optional processing steps for the palpation algorithms. Memory 44 can be any type of storage device or computer readable medium capable of storing the instructions for palpation algorithms 46. Memory 44 can include random access memory, read-only memory, etc. In some embodiments, processor 42 can be an application specific integrated circuit (ASIC) that is a component of the tool. In other embodiments, the instructions for palpation algorithms 46 can be embedded in processor 42.

In some embodiments, sensor array 40 can include a 2×7 array of pressure transducers. Each pressure transducer can be in contact with the tissue being palpated, therefore, each transducer is processed for pulses received. Each transducer can detect zero or more pulses in a predetermined time window. Actuator 48 can generate a vibration on the handle of the tool. More specifically, the actuator 48 can include a force applying mechanism that applies a vibrotactile force to the tool based on a level of stiffness or deformation of the tissue being examined. One parameter of the actuator that can be used in some embodiments is the peak voltage applied during the playing of haptic effects.

Figure 5:
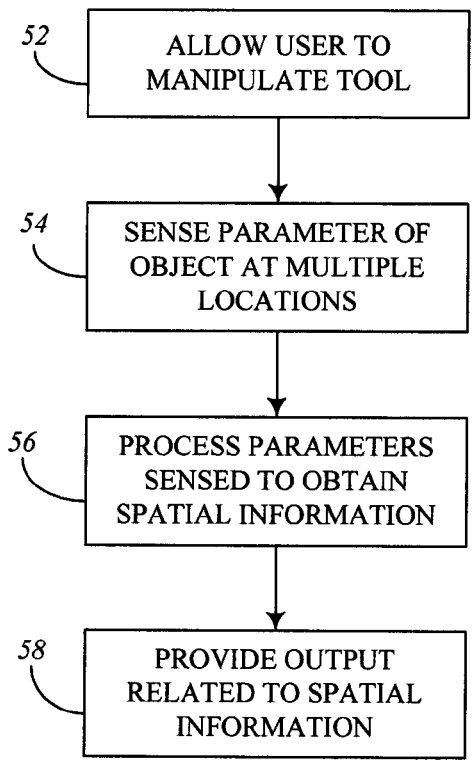
FIG. 5 is a flow diagram illustrating a method for operating an array of sensors on a tool, according to one embodiment.

FIG. 5 is a flow diagram of an embodiment of a method of operating a tool having a sensor array. As indicated in block 52, a user is allowed to manipulate a tool according to a normal use of the tool. For example, the user may manipulate a handle, buttons, or other feature on the tool to control a functional portion of the tool. The controlled portion may be a portion that is positioned on an opposite end from the handle. The controlled portion can be probed around to contact an object being tested or to be placed in proximity to the object being tested, depending on the particular type of parameter being measured.

As indicated in block 54, a parameter of the object is sensed at multiple locations. Particularly, the multiple locations may represent the positioning of a number of sensors mounted on or relative to the tool, such as sensors that may be positioned on or near the controlled portion of the tool. In some embodiments, the sensing locations may form a predefined pattern, such as a rectangular array having rows and columns. In other embodiments, the sensing locations may include any other suitable pattern.

According to block 56 of the method of FIG. 4, the sensed properties are processed to obtain spatial information about the object being tested. Based on the properties sensed at the multiple locations and based on a predetermined knowledge of the location and orientation of the sensors, spatial information can be obtained. In some embodiments in which the object being tested is a surgical patient, the sensed properties may be related to the blood of the patient. For example, if pulse information is detected at some sensor locations, the sensed information can be processed to determine the location and orientation of blood vessels of the patient.

Furthermore, the spatial information can also be obtained by processing the information at regular time intervals, allowing both spatial and temporal information to be obtained. Again referring to the blood of a patient, the spatiotemporal information can be used to determine not only the location and orientation of the blood vessels, but also the direction in which the blood flows through the blood vessels. In this respect, a signal may be strong at one sensor location at one time and, after a short delay, the signal may be strong at another sensor location, thereby indicating the flow direction. The processing associated with block 46 is able to decode the sensed information from the multiple locations at multiple times to compute the spatial and/or spatiotemporal information.

As indicated in block 58, an output is provided to the user to indicate the spatial information. As suggested above, when spatiotemporal information is also calculated, this information can also be output to the user. The output may be presented in any suitable form. For example, the output may be a haptic or tactile effect imposed on the user. In some embodiments, the output may be haptic, audible, and/or visual. Any suitable combination of output mechanisms or actuators can be used to present the output. With respect to some embodiments, haptic actuators can be arranged in an array or other pattern resembling the array or pattern of the sensors. In this case, the sensed signals can be mapped to provide a haptic effect to represent the spatial information sensed by the sensors.

It should be understood that the routines, steps, processes, or operations described herein may represent any module or code sequence that can be implemented in software or firmware. In this regard, these modules and code sequences can include commands or instructions for executing the specific logical routines, steps, processes, or operations within physical components. It should further be understood that two or more of the routines, steps, processes, and/or operations described herein may be executed substantially simultaneously or in a different order than explicitly described, as would be understood by one of ordinary skill in the art.

The embodiments described herein represent a number of possible implementations and examples and are not necessarily intended to limit the present disclosure to any specific embodiments. Instead, various modifications can be made to these embodiments as would be understood by one of ordinary skill in the art. Any such modifications are intended to be included within the spirit and scope of the present disclosure and encompassed within the following claims.

We claim:

1. A surgical hand tool comprising:
   an end portion configured to perform a function;
   a handle portion that, when manipulated by a user, causes the end portion to perform its function;
   a plurality of sensors on the end portion arranged in a predetermined spatial array to concurrently sense a property of a patient at multiple locations;
   a processing device coupled to receive signals from the plurality of sensors and programmed to process the signals to obtain spatiotemporal information about blood flow of the patient by processing the property sensed over time, wherein the spatiotemporal information comprises information about a direction of blood flow through a blood vessel of the patient; and
   an output device configured to present the spatiotemporal information about blood flow of the patient to the user;
   wherein the output device is a haptic actuator configured to impose a haptic effect on the user, the haptic effect being related to the spatiotemporal information obtained by the processing device.

2. The tool of claim 1, wherein the property being sensed is a pulse of the patient.

3. The tool of claim 1, wherein the surgical hand tool is a laparoscopic tool.

4. The tool of claim 1, wherein the processing device is further programmed to process the signals to obtain spatial information of a location and orientation of a luminal structure of the patient.

5. The tool of claim 4, wherein the luminal structure is a blood vessel.

6. The tool of claim 1, wherein the end portion comprises a rigid substrate on which the array of sensors is mounted.

7. The tool of claim 1, wherein the end portion comprises a flexible substrate on which the array of sensors is mounted.

8. The tool of claim 1, wherein the predetermined spatial array of sensors comprises at least two rows of sensors and at least two columns of sensors arranged in a substantially rectangular pattern.

9. The tool of claim 1, wherein at least one sensor of the predetermined spatial array of sensors is configured to sense pressure.

10. The tool of claim 1, wherein at least one sensor of the array of sensors is a piezoelectric sensor.

11. The tool of claim 10, wherein the at least one piezoelectric sensor is configured to emanate ultrasound radiation and measure echo information.

12. The tool of claim 1, wherein the haptic actuator is configured to impose vibrotactile feedback to the user.

13. The tool of claim 1, wherein the processing device resides in the handle portion.

14. A surgical hand tool comprising:
   means for concurrently sensing a characteristic related to blood of a patient at multiple proximate locations of an internal region of the patient;
   means for processing the characteristic related to blood of the patient concurrently sensed at the multiple proximate locations to obtain spatial information about the blood of the patient, wherein the spatial information about the blood of the patient is related to the location and orientation of one or more blood vessels with respect to the surgical hand tool; and
   means for providing an output indicative of the location and orientation of the one or more blood vessels with respect to the surgical hand tool.

15. The surgical hand tool of claim 14, wherein the means for concurrently sensing is configured to sense the characteristic at an array of locations, wherein the array comprises at least two rows and at least two columns.

16. The surgical hand tool of claim 14, wherein the means for processing is further configured to obtain spatiotemporal information about the blood of the patient by processing the characteristic sensed at the multiple proximate locations over time.

17. The surgical hand tool of claim 16, wherein the spatiotemporal information is related to the direction of blood flow through the one or more blood vessels.

* * * * *